United States Patent
Haas et al.

(10) Patent No.: US 10,265,602 B2
(45) Date of Patent: Apr. 23, 2019

(54) AIMING FEEDBACK SYSTEM WITH INERTIAL SENSORS

(71) Applicant: BLAST MOTION INC., Burlingame, CA (US)

(72) Inventors: Juergen Haas, Poway, CA (US);
Bhaskar Bose, Carlsbad, CA (US);
Michael Bentley, Carlsbad, CA (US);
Piyush Gupta, Vista, CA (US);
Sheehan Alam, Ukiah, CA (US); Ryan Gullotti, Vista, CA (US)

(73) Assignee: BLAST MOTION INC., Carlsbad, CA (US)

( * ) Notice: Subject to any disclaimer, the term of this patent is extended or adjusted under 35 U.S.C. 154(b) by 12 days.

(21) Appl. No.: 15/060,217

(22) Filed: Mar. 3, 2016

(65) Prior Publication Data
US 2017/0252607 A1 Sep. 7, 2017

(51) Int. Cl.
*A63B 69/36* (2006.01)
*A63B 71/06* (2006.01)
(Continued)

(52) U.S. Cl.
CPC .......... *A63B 71/0619* (2013.01); *A61B 5/681* (2013.01); *A63B 69/36* (2013.01);
(Continued)

(58) Field of Classification Search
CPC ............ A63B 24/0006; A63B 24/0012; A63B 69/3614; A63B 69/3632; A63B 71/0619
See application file for complete search history.

(56) References Cited

U.S. PATENT DOCUMENTS

| 1,712,537 | A | 5/1929 | White |
| 3,182,508 | A | 5/1965 | Varju |

(Continued)

FOREIGN PATENT DOCUMENTS

| EP | 2025369 | 2/2009 |
| JP | 2002210055 A | 7/2002 |

(Continued)

OTHER PUBLICATIONS

Patent Examination Report received in Australia Application No. 2011313952, dated Mar. 15, 2016, 5 pages.
(Continued)

*Primary Examiner* — David Duffy
(74) *Attorney, Agent, or Firm* — Arc IP Law, PC; Joseph J. Mayo

(57) ABSTRACT

An aiming system that provides feedback on how closely the aim of an object is aligned with a direction to a target. An inertial sensor on the object provides data on the object's position and orientation; this data is combined with target direction information to determine how to correct the aim. An illustrative application is a golf club aiming system that measures whether the clubface normal is aligned horizontally with the direction to the hole. The system sends feedback signals to the user to help the user adjust the aim. These signals may include for example audible tones or haptic vibrations that vary in frequency and amplitude to instruct the user to adjust the aim. For example, haptic signals may be sent to a smart watch worn by the user; the user may therefore obtain aiming feedback without having to look at a screen.

19 Claims, 9 Drawing Sheets

US 10,265,602 B2

Page 2

(51) Int. Cl.
*A63B 69/38* (2006.01)
*A61B 5/00* (2006.01)

(52) U.S. Cl.
CPC ...... *A63B 69/38* (2013.01); *A63B 2071/0625* (2013.01); *A63B 2071/0655* (2013.01); *A63B 2220/12* (2013.01); *A63B 2220/40* (2013.01); *A63B 2220/803* (2013.01); *A63B 2225/50* (2013.01); *G08C 2201/93* (2013.01)

(56) References Cited

U.S. PATENT DOCUMENTS

| | | | |
|---|---|---|---|
| 3,226,704 A | 12/1965 | Petrash | |
| 3,270,564 A | 9/1966 | Evans | |
| 3,776,556 A * | 12/1973 | McLaughlin | A63B 69/3635 446/216 |
| 3,788,647 A | 1/1974 | Evans | |
| 3,792,863 A | 2/1974 | Evans | |
| 3,806,131 A | 4/1974 | Evans | |
| 3,945,646 A | 3/1976 | Hammond | |
| 4,759,219 A | 7/1988 | Cobb et al. | |
| 4,902,014 A | 2/1990 | Bontomase et al. | |
| 4,910,677 A | 3/1990 | Remedio et al. | |
| 4,898,389 A | 6/1990 | Plutt | |
| 4,940,236 A | 10/1990 | Allen | |
| 4,991,850 A | 2/1991 | Wilhlem | |
| 5,056,783 A | 10/1991 | Matcovich et al. | |
| 5,086,390 A | 4/1992 | Matthews | |
| 5,111,410 A | 5/1992 | Nakayama et al. | |
| 5,127,044 A | 6/1992 | Bonito et al. | |
| 5,184,295 A | 2/1993 | Mann | |
| 5,230,512 A | 7/1993 | Tattershall | |
| 5,233,544 A | 8/1993 | Kobayashi | |
| 5,249,967 A | 10/1993 | O'Leary et al. | |
| 5,259,620 A | 11/1993 | Marocco | |
| 5,283,733 A | 1/1994 | Colley | |
| 5,298,904 A | 3/1994 | Olich | |
| 5,332,225 A | 7/1994 | Ura | |
| 5,333,061 A | 7/1994 | Nakashima et al. | |
| 5,364,093 A | 11/1994 | Huston et al. | |
| 5,372,365 A | 12/1994 | McTeigue et al. | |
| 5,441,256 A | 8/1995 | Hackman | |
| 5,441,269 A | 8/1995 | Henwood | |
| 5,443,260 A | 8/1995 | Stewart et al. | |
| 5,486,001 A | 1/1996 | Baker | |
| 5,524,081 A | 4/1996 | Paul | |
| 5,542,676 A | 8/1996 | Howe et al. | |
| 5,592,401 A | 1/1997 | Kramer | |
| 5,610,590 A | 3/1997 | Johnson et al. | |
| 5,638,300 A | 6/1997 | Johnson | |
| 5,665,006 A | 9/1997 | Pellegrini | |
| 5,688,183 A | 11/1997 | Sabatino et al. | |
| 5,694,340 A | 12/1997 | Kim | |
| 5,707,299 A * | 1/1998 | McKenna | A63B 69/3685 473/241 |
| 5,772,522 A | 6/1998 | Nesbit | |
| 5,779,555 A | 7/1998 | Nomura et al. | |
| 5,819,206 A | 10/1998 | Horton | |
| 5,826,578 A | 10/1998 | Curchod | |
| 5,792,001 A | 11/1998 | Henwood | |
| 5,868,578 A | 2/1999 | Baum | |
| 5,904,484 A | 5/1999 | Burns | |
| 5,941,779 A | 8/1999 | Zeiner-Gundersen | |
| 5,973,596 A | 10/1999 | French et al. | |
| 5,993,333 A * | 11/1999 | Heckaman | A63B 69/3614 473/220 |
| 5,998,968 A | 12/1999 | Pittman et al. | |
| 6,012,995 A | 1/2000 | Martin | |
| 6,030,109 A | 2/2000 | Lobsenz | |
| 6,044,704 A | 4/2000 | Sacher | |
| 6,073,086 A | 6/2000 | Marinelli | |
| 6,224,493 B1 | 5/2001 | Lee et al. | |
| 6,248,021 B1 | 6/2001 | Ognjanovic | |
| 6,253,159 B1 | 6/2001 | Bett et al. | |
| 6,254,492 B1 | 7/2001 | Taggett | |
| 6,266,623 B1 | 7/2001 | Vock et al. | |
| 6,293,802 B1 | 9/2001 | Ahlgren | |
| 6,366,205 B1 | 4/2002 | Sutphen | |
| 6,441,745 B1 | 8/2002 | Gates | |
| 6,456,938 B1 | 9/2002 | Barnard | |
| 6,537,076 B2 | 3/2003 | McNitt | |
| 6,540,620 B1 | 4/2003 | Consiglio | |
| 6,567,536 B2 | 5/2003 | McNitt | |
| 6,582,328 B2 | 6/2003 | Kuta et al. | |
| 6,611,141 B1 | 8/2003 | Schulz | |
| 6,697,820 B1 | 2/2004 | Tarlie | |
| 6,705,942 B1 | 3/2004 | Crook et al. | |
| 6,746,336 B1 | 6/2004 | Brant et al. | |
| 6,757,572 B1 | 6/2004 | Forest | |
| 6,774,932 B1 | 8/2004 | Ewing et al. | |
| 6,802,772 B1 | 12/2004 | Kunzle et al. | |
| 6,923,729 B2 | 2/2005 | McGinty et al. | |
| 6,868,338 B1 | 3/2005 | Elliott | |
| 6,900,759 B1 | 5/2005 | Katayama | |
| 6,908,404 B1 | 6/2005 | Gard | |
| 7,004,848 B2 | 2/2006 | Konow | |
| 7,037,198 B2 | 2/2006 | Hameen-Antilla | |
| 7,021,140 B2 | 4/2006 | Perkins | |
| 7,034,694 B2 | 4/2006 | Yamaguchi et al. | |
| 7,143,639 B2 | 5/2006 | Gobush | |
| 7,092,846 B2 | 8/2006 | Vock et al. | |
| 7,118,498 B2 | 10/2006 | Meadows et al. | |
| 7,121,962 B2 | 10/2006 | Reeves | |
| 7,175,177 B2 | 2/2007 | Meifu et al. | |
| 7,205,894 B1 | 4/2007 | Savage | |
| 7,212,943 B2 | 5/2007 | Aoshima et al. | |
| 7,219,033 B2 | 5/2007 | Kolen | |
| 7,234,351 B2 | 6/2007 | Perkins | |
| 7,160,200 B2 | 9/2007 | Grober | |
| 7,264,554 B2 | 9/2007 | Bentley | |
| 7,283,647 B2 | 10/2007 | Mcnitt | |
| 7,433,805 B2 | 7/2008 | Vock et al. | |
| 7,421,369 B2 | 9/2008 | Clarkson | |
| 7,457,439 B1 | 11/2008 | Madsen | |
| 7,457,724 B2 | 11/2008 | Vock et al. | |
| 7,492,367 B2 | 2/2009 | Mahajan et al. | |
| 7,494,236 B2 | 2/2009 | Lim | |
| 7,499,828 B2 | 3/2009 | Barton | |
| 7,561,989 B2 | 7/2009 | Banks | |
| 7,623,987 B2 | 11/2009 | Vock et al. | |
| 7,627,451 B2 | 12/2009 | Vock et al. | |
| 7,689,378 B2 | 3/2010 | Kolen | |
| 7,713,148 B2 | 5/2010 | Sweeney | |
| 7,731,598 B1 * | 6/2010 | Kim | A63B 57/00 473/226 |
| 7,736,242 B2 | 6/2010 | Stites et al. | |
| 7,771,263 B2 | 8/2010 | Telford | |
| 7,780,450 B2 | 8/2010 | Tarry | |
| 7,800,480 B1 | 9/2010 | Joseph et al. | |
| 7,813,887 B2 | 10/2010 | Vock et al. | |
| 7,831,212 B1 | 11/2010 | Balardeta et al. | |
| 7,871,333 B1 | 1/2011 | Davenport | |
| 7,966,154 B2 | 6/2011 | Vock et al. | |
| 7,983,876 B2 | 7/2011 | Vock et al. | |
| 8,036,826 B2 | 11/2011 | MacIntosh et al. | |
| 8,117,888 B2 | 2/2012 | Chan et al. | |
| 8,172,722 B2 | 5/2012 | Molyneux et al. | |
| 8,231,506 B2 | 7/2012 | Molyneux et al. | |
| 8,246,050 B2 * | 8/2012 | Do | A63D 15/006 273/317 |
| 8,249,831 B2 | 8/2012 | Vock et al. | |
| 8,257,191 B2 | 9/2012 | Stites et al. | |
| 8,282,487 B2 | 10/2012 | Wilson et al. | |
| 8,314,840 B1 | 11/2012 | Funk | |
| 8,352,211 B2 | 1/2013 | Vock et al. | |
| 8,400,548 B2 | 3/2013 | Bilbrey et al. | |
| 8,425,292 B2 | 4/2013 | Lui et al. | |
| 8,477,027 B2 | 7/2013 | Givens | |
| 8,527,228 B2 | 9/2013 | Panagas | |
| 8,565,483 B2 | 10/2013 | Nakaoka | |
| 8,589,114 B2 | 11/2013 | Papadourakis | |
| 8,696,482 B1 | 4/2014 | Pedenko et al. | |
| 8,723,986 B1 | 5/2014 | Merrill | |
| 8,725,452 B2 | 5/2014 | Han | |

(56) References Cited

U.S. PATENT DOCUMENTS

| | | |
|---|---|---|
| 8,764,576 B2 | 7/2014 | Takasugi |
| 8,781,610 B2 | 7/2014 | Han |
| 8,831,905 B2 | 9/2014 | Papadourakis |
| 8,876,621 B2 | 11/2014 | Shibuya |
| 8,888,603 B2 | 11/2014 | Sato et al. |
| 8,905,856 B2 * | 12/2014 | Parke .................. G01P 15/0888 473/223 |
| 8,929,709 B2 | 1/2015 | Lokshin |
| 8,944,932 B2 | 2/2015 | Sato et al. |
| 8,944,939 B2 | 2/2015 | Clark et al. |
| 8,956,238 B2 | 2/2015 | Boyd et al. |
| 8,988,341 B2 | 3/2015 | Lin et al. |
| 8,989,441 B2 | 3/2015 | Han et al. |
| 9,032,794 B2 | 5/2015 | Perkins et al. |
| 9,060,682 B2 | 6/2015 | Lokshin |
| 9,146,134 B2 | 9/2015 | Lokshin et al. |
| 9,395,385 B2 * | 7/2016 | Parke .................. G01P 15/0888 |
| 9,656,122 B2 | 5/2017 | Papadourakis |
| 9,694,267 B1 | 7/2017 | Thornbrue et al. |
| 2001/0035880 A | 1/2001 | Musatov et al. |
| 2001/0049636 A1 | 6/2001 | Hudda et al. |
| 2001/0029207 A1 | 10/2001 | Cameron et al. |
| 2001/0045904 A1 | 11/2001 | Silzer, Jr. |
| 2002/0019677 A1 | 2/2002 | Lee |
| 2002/0052750 A1 | 2/2002 | Hirooka |
| 2002/0049507 A1 | 4/2002 | Hameen-Anttila |
| 2002/0064764 A1 | 5/2002 | Fishman |
| 2002/0072815 A1 | 6/2002 | McDonough et al. |
| 2002/0077189 A1 | 6/2002 | Tuer et al. |
| 2002/0082775 A1 | 6/2002 | Meadows et al. |
| 2002/0115046 A1 | 8/2002 | McNitt et al. |
| 2002/0126157 A1 | 9/2002 | Farago et al. |
| 2002/0004723 A1 | 10/2002 | Meifu et al. |
| 2002/0151994 A1 | 10/2002 | Sisco |
| 2002/0173364 A1 | 11/2002 | Boscha |
| 2002/0177490 A1 | 11/2002 | Yong et al. |
| 2002/0188359 A1 | 12/2002 | Morse |
| 2003/0073518 A1 | 4/2003 | Marty |
| 2003/0074659 A1 | 4/2003 | Louzoun |
| 2003/0109322 A1 | 6/2003 | Funk et al. |
| 2003/0163287 A1 | 8/2003 | Vock et al. |
| 2003/0008722 A1 | 9/2003 | Konow |
| 2003/0191547 A1 | 9/2003 | Morse |
| 2003/0208830 A1 | 11/2003 | Marmaropoulos |
| 2004/0028258 A1 | 2/2004 | Naimark et al. |
| 2004/0033843 A1 | 2/2004 | Miller |
| 2004/0044493 A1 | 3/2004 | Coulthard |
| 2004/0147329 A1 | 7/2004 | Meadows et al. |
| 2004/0227676 A1 | 11/2004 | Kim et al. |
| 2004/0248676 A1 | 12/2004 | Taylor |
| 2005/0021292 A1 | 1/2005 | Vock et al. |
| 2005/0023763 A1 | 2/2005 | Richardson |
| 2005/0032582 A1 | 2/2005 | Mahajan et al. |
| 2005/0054457 A1 | 3/2005 | Eyestone et al. |
| 2005/0156068 A1 | 7/2005 | Ivans |
| 2005/0268704 A1 | 8/2005 | Bissonnette et al. |
| 2005/0272516 A1 | 8/2005 | Gobush |
| 2005/0203430 A1 | 9/2005 | Williams et al. |
| 2005/0213076 A1 | 9/2005 | Saegusa |
| 2005/0215340 A1 | 9/2005 | Stites et al. |
| 2005/0227775 A1 | 10/2005 | Cassady et al. |
| 2005/0261073 A1 | 11/2005 | Farrington, Jr. et al. |
| 2005/0282650 A1 | 12/2005 | Miettinen et al. |
| 2005/0288119 A1 | 12/2005 | Wang et al. |
| 2006/0020177 A1 | 1/2006 | Seo et al. |
| 2006/0025229 A1 | 2/2006 | Mahajan et al. |
| 2006/0038657 A1 | 2/2006 | Denison et al. |
| 2006/0063600 A1 | 3/2006 | Grober |
| 2006/0068928 A1 | 3/2006 | Nagy |
| 2006/0084516 A1 | 4/2006 | Eyestone et al. |
| 2006/0109116 A1 | 5/2006 | Keays |
| 2006/0122002 A1 | 6/2006 | Konow |
| 2006/0166738 A1 | 7/2006 | Eyestone et al. |
| 2006/0199659 A1 | 7/2006 | Caldwell |
| 2006/0276256 A1 | 7/2006 | Storek |
| 2006/0189389 A1 | 8/2006 | Hunter et al. |
| 2006/0247070 A1 | 11/2006 | Funk et al. |
| 2006/0250745 A1 | 11/2006 | Butler et al. |
| 2006/0270450 A1 | 11/2006 | Garratt et al. |
| 2006/0284979 A1 | 12/2006 | Clarkson |
| 2006/0293112 A1 * | 12/2006 | Yi ..................... A63B 53/0466 473/241 |
| 2007/0062284 A1 | 3/2007 | Machida |
| 2007/0081695 A1 | 4/2007 | Foxlin et al. |
| 2007/0087866 A1 | 4/2007 | Meadows et al. |
| 2007/0099715 A1 | 5/2007 | Jones et al. |
| 2007/0111811 A1 | 5/2007 | Grober |
| 2007/0135225 A1 | 6/2007 | Nieminen |
| 2007/0135237 A1 | 6/2007 | Reeves |
| 2007/0129178 A1 | 7/2007 | Reeves |
| 2007/0052807 A1 | 8/2007 | Zhou et al. |
| 2007/0219744 A1 | 9/2007 | Kolen |
| 2007/0265105 A1 | 11/2007 | Barton |
| 2007/0270214 A1 | 11/2007 | Bentley |
| 2007/0298753 A1 | 12/2007 | Tary et al. |
| 2007/0298896 A1 | 12/2007 | Nusbaum |
| 2008/0027502 A1 | 1/2008 | Ransom |
| 2008/0085778 A1 | 4/2008 | Dugan |
| 2008/0090703 A1 | 4/2008 | Rosenberg |
| 2008/0108456 A1 | 5/2008 | Bonito |
| 2008/0164999 A1 | 7/2008 | Otto |
| 2008/0182685 A1 * | 7/2008 | Marty ................ A63B 24/0003 473/407 |
| 2008/0190202 A1 | 8/2008 | Kulach et al. |
| 2008/0234935 A1 | 9/2008 | Wolf et al. |
| 2008/0280642 A1 | 11/2008 | Coxhill et al. |
| 2008/0284979 A1 | 11/2008 | Yee et al. |
| 2008/0285805 A1 | 11/2008 | Luinge et al. |
| 2009/0002316 A1 | 1/2009 | Rofougaran |
| 2009/0017944 A1 | 1/2009 | Savarese et al. |
| 2009/0029754 A1 | 1/2009 | Slocum et al. |
| 2009/0033741 A1 | 2/2009 | Oh et al. |
| 2009/0036237 A1 | 2/2009 | Nipper et al. |
| 2009/0048044 A1 | 2/2009 | Oleson et al. |
| 2009/0055820 A1 | 2/2009 | Huang |
| 2009/0088276 A1 | 4/2009 | Solheim et al. |
| 2009/0111602 A1 | 4/2009 | Savarese et al. |
| 2009/0131190 A1 | 5/2009 | Kimber |
| 2009/0137333 A1 | 5/2009 | Lin et al. |
| 2009/0174676 A1 | 7/2009 | Westerman |
| 2009/0177097 A1 | 7/2009 | Ma et al. |
| 2009/0191846 A1 | 7/2009 | Shi |
| 2009/0209343 A1 | 8/2009 | Foxlin et al. |
| 2009/0209358 A1 | 8/2009 | Niegowski |
| 2009/0213134 A1 | 8/2009 | Stephanick et al. |
| 2009/0222163 A1 | 9/2009 | Plante |
| 2009/0233735 A1 | 9/2009 | Savarese et al. |
| 2009/0254276 A1 | 10/2009 | Faulkner et al. |
| 2009/0254971 A1 | 10/2009 | Herz et al. |
| 2009/0299232 A1 | 12/2009 | Lanfermann et al. |
| 2010/0049468 A1 | 2/2010 | Papadourakis |
| 2010/0062869 A1 | 3/2010 | Chung et al. |
| 2010/0091112 A1 | 4/2010 | Veeser et al. |
| 2010/0093458 A1 | 4/2010 | Davenport et al. |
| 2010/0099509 A1 | 4/2010 | Ahem et al. |
| 2010/0103269 A1 | 4/2010 | Wilson et al. |
| 2010/0113174 A1 | 5/2010 | Ahern |
| 2010/0121227 A1 | 5/2010 | Stirling et al. |
| 2010/0121228 A1 | 5/2010 | Stirling et al. |
| 2010/0130298 A1 | 5/2010 | Dugan et al. |
| 2010/0144414 A1 | 6/2010 | Edis et al. |
| 2010/0144456 A1 | 6/2010 | Ahern |
| 2010/0144457 A1 * | 6/2010 | Kim .................... A63B 57/00 473/226 |
| 2010/0178994 A1 * | 7/2010 | Do ..................... A63D 15/006 473/2 |
| 2010/0201512 A1 | 8/2010 | Stirling et al. |
| 2010/0204616 A1 | 8/2010 | Shears et al. |
| 2010/0216564 A1 | 8/2010 | Stites et al. |
| 2010/0222152 A1 | 9/2010 | Jaekel et al. |
| 2010/0063778 A1 | 11/2010 | Schrock et al. |
| 2010/0063779 A1 | 11/2010 | Schrock et al. |
| 2010/0308105 A1 | 12/2010 | Savarese et al. |

(56) References Cited

U.S. PATENT DOCUMENTS

| | | | |
|---|---|---|---|
| 2010/0309097 A1* | 12/2010 | Raviv | A63F 13/53 345/8 |
| 2010/0323794 A1 | 12/2010 | Su | |
| 2011/0004871 A1 | 1/2011 | Liu | |
| 2011/0029235 A1 | 2/2011 | Berry | |
| 2011/0037778 A1 | 2/2011 | Deng et al. | |
| 2011/0050864 A1 | 3/2011 | Bond | |
| 2011/0052005 A1 | 3/2011 | Selner | |
| 2011/0053688 A1 | 3/2011 | Crawford | |
| 2011/0075341 A1 | 3/2011 | Lau et al. | |
| 2011/0081981 A1 | 4/2011 | Okamoto | |
| 2011/0126184 A1 | 5/2011 | Lisboa | |
| 2011/0165998 A1 | 7/2011 | Lau et al. | |
| 2011/0195780 A1 | 8/2011 | Lu | |
| 2011/0230273 A1 | 9/2011 | Niegowski et al. | |
| 2011/0230274 A1 | 9/2011 | Lafortune et al. | |
| 2011/0230985 A1 | 9/2011 | Niegowski et al. | |
| 2011/0230986 A1 | 9/2011 | Lafortune | |
| 2011/0238308 A1 | 9/2011 | Miller et al. | |
| 2011/0305369 A1 | 12/2011 | Bentley | |
| 2012/0023354 A1 | 1/2012 | Chino | |
| 2012/0052972 A1 | 3/2012 | Bentley | |
| 2012/0115626 A1 | 5/2012 | Davenport | |
| 2012/0115682 A1 | 5/2012 | Homsi | |
| 2012/0116548 A1 | 5/2012 | Goree et al. | |
| 2012/0120572 A1 | 5/2012 | Bentley | |
| 2012/0157241 A1 | 6/2012 | Nomura et al. | |
| 2012/0179418 A1 | 7/2012 | Takasugi et al. | |
| 2012/0179742 A1 | 7/2012 | Acharya et al. | |
| 2012/0191405 A1 | 7/2012 | Molyneux et al. | |
| 2012/0295726 A1 | 11/2012 | Cherbini | |
| 2012/0316004 A1 | 12/2012 | Shibuya | |
| 2013/0029791 A1 | 1/2013 | Rose et al. | |
| 2013/0095941 A1 | 4/2013 | Bentley et al. | |
| 2013/0110415 A1 | 5/2013 | Davis et al. | |
| 2013/0128022 A1 | 5/2013 | Bose et al. | |
| 2013/0173212 A1 | 7/2013 | Saiki et al. | |
| 2013/0178304 A1 | 7/2013 | Chan | |
| 2013/0191063 A1 | 7/2013 | Nomura | |
| 2013/0225309 A1 | 8/2013 | Bentley et al. | |
| 2013/0267335 A1* | 10/2013 | Boyd | A63B 69/36 473/222 |
| 2013/0271602 A1 | 10/2013 | Bentley et al. | |
| 2013/0298668 A1 | 11/2013 | Sato | |
| 2013/0319113 A1 | 12/2013 | Mizuta | |
| 2013/0330054 A1 | 12/2013 | Lokshin | |
| 2013/0332004 A1 | 12/2013 | Gompert et al. | |
| 2013/0346013 A1 | 12/2013 | Lokshin | |
| 2014/0019083 A1 | 1/2014 | Nakaoka | |
| 2014/0100048 A1 | 4/2014 | Ota et al. | |
| 2014/0100049 A1 | 4/2014 | Ota et al. | |
| 2014/0100050 A1 | 4/2014 | Ota et al. | |
| 2014/0135139 A1 | 5/2014 | Shibuya et al. | |
| 2014/0156214 A1 | 6/2014 | Nomura | |
| 2014/0172873 A1 | 6/2014 | Varoglu et al. | |
| 2014/0200092 A1* | 7/2014 | Parke | G01P 15/0888 473/223 |
| 2014/0200094 A1 | 7/2014 | Parke et al. | |
| 2014/0229135 A1 | 8/2014 | Nomura | |
| 2014/0229138 A1 | 8/2014 | Goree et al. | |
| 2014/0257743 A1 | 9/2014 | Lokshin et al. | |
| 2014/0257744 A1 | 9/2014 | Lokshin et al. | |
| 2014/0295982 A1 | 10/2014 | Shibuya | |
| 2014/0376876 A1 | 12/2014 | Bentley et al. | |
| 2014/0378239 A1 | 12/2014 | Sato et al. | |
| 2014/0379293 A1 | 12/2014 | Sato | |
| 2014/0379294 A1 | 12/2014 | Shibuya et al. | |
| 2014/0379295 A1 | 12/2014 | Sato et al. | |
| 2015/0007658 A1 | 1/2015 | Ishikawa et al. | |
| 2015/0012240 A1 | 1/2015 | Sato | |
| 2015/0042481 A1 | 2/2015 | Nomura | |
| 2015/0098688 A1 | 4/2015 | Lokshin | |
| 2015/0107358 A1* | 4/2015 | Parke | G01P 15/0888 73/514.02 |
| 2015/0124048 A1 | 5/2015 | King | |
| 2015/0126308 A1* | 5/2015 | Penn | A63B 69/36 473/407 |
| 2015/0131845 A1 | 5/2015 | Forouhar et al. | |
| 2015/0154452 A1 | 6/2015 | Bentley et al. | |
| 2015/0256689 A1 | 9/2015 | Erkkila et al. | |
| 2015/0348591 A1 | 12/2015 | Kaps et al. | |
| 2016/0354668 A1* | 12/2016 | Cho | A63B 69/3608 |
| 2017/0061817 A1* | 3/2017 | Mettler May | G09B 19/003 |

FOREIGN PATENT DOCUMENTS

| | | |
|---|---|---|
| JP | 2004207985 | 7/2004 |
| JP | 10-2006-0041060 | 5/2006 |
| JP | 2011000367 | 6/2011 |
| JP | 2012196241 | 10/2012 |
| KR | 10-20030085275 | 11/2003 |
| KR | 10-2007-0119018 | 12/2007 |
| KR | 10-20100020131 | 2/2010 |
| KR | 10-20100074068 | 7/2010 |
| KR | 10-1079319 | 4/2011 |
| WO | 94/27683 | 8/1994 |
| WO | 2007130057 A1 | 11/2007 |
| WO | 2009056688 A1 | 5/2009 |
| WO | 2011057194 | 5/2011 |
| WO | 2014085744 A1 | 6/2014 |

OTHER PUBLICATIONS

"About Banjo" retrieved from the internet, dated 2015.
International Search Report received in PCT/US2016/042668, dated Oct. 4, 2016, 21 pages.
International Search Report received in PCT/US2016/042671, dated Oct. 13, 2016, 17 pages.
International Search Report and Written Opinion received in PCT/US2016/042676, dated Oct. 24, 2016 (12 pages).
International Preliminary Report on Patentability received in PCT/US2015/026917, dated Nov. 3, 2016 (5 pages).
International Preliminary Report on Patentability in PCTUS2015061695 (our matter 19007-P082-PCT), on Jun. 1, 2017, 5 pages.
European Search Report received in PCTUS2015026896 on May 11, 2017, 13 pages.
Zepp Labs, Inc. v. Blast Motion, Inc. Petition for Inter Partes Review of U.S. Pat. No. 8,903,521 filed on Feb. 24, 2016, as IPR2016-00672, and accompanying Declaration of Dr. Steven M. Nesbit.
Zepp Labs, Inc. v. Blast Motion, Inc. Petition for Inter Partes Review of U.S. Pat. No. 9,039,527 filed on Feb. 24, 2016, as IPR2016-00674, and accompanying Declaration of Dr. Steven M. Nesbit.
Zepp Labs, Inc. v. Blast Motion, Inc. Petition for Inter Partes Review of U.S. Pat. No. 8,941,723 filed on Feb. 24, 2016, as IPR2016-00675, and accompanying Declaration of Dr. Steven M. Nesbit.
Zepp Labs, Inc. v. Blast Motion, Inc. Petition for Inter Partes Review of U.S. Pat. No. 8,905,855 filed on Feb. 24, 2016, as IPR2016-00676, and accompanying Declaration of Dr. Steven M. Nesbit.
Zepp Labs, Inc. v. Blast Motion, Inc. Petition for Inter Partes Review of U.S. Pat. No. 8,944,928 filed on Feb. 24, 2016, as IPR2016-00677, and accompanying Declaration of Dr. Steven M. Nesbit.
Chris Otto, et al, "System Architecture of a Wireless Body Area Sensor Network for Ubiquitous Health Monitoring", *Journal of Mobile Multimedia*, vol. 1, No. 4, Jan. 10, 2006, University of Alabama in Huntsville, 20 Pages.
Linx Technologies "High Performance RF Module: Hp3 Series Transmitter Module Data Guide Description", Jul. 27, 2011, 13 pages.
Roger Allan, "Wireless Sensor Architectures Uses Bluetooth Standard", www.electronicdesign.com/communications/wireless-sensor-architecture-uses-bluetooth-standard, Aug. 7, 2000, 5 pages.
Don Tuite, "Motion-Sensing MEMS Gyros and Accelerometers are Everywhere", www.electronicdesign.com/print/analog/motion-sensing-mems-gyros-and-accelerometers-are-everywhere, Jul. 9, 2009, 6 pages.
InvenSense News Release, "InvenSense Unveils World's 1$^{st}$ IMU Solution for Consumer Applications", ir.invensense.com, 2016, 2 Pages.

(56) References Cited

OTHER PUBLICATIONS

Dean Takahashi, "Facebook, Twitter, Last.fm coming to Xbox Live this Fall", Jun. 1, 2009, Webpage printout, 5 pages.
The iClub System, Products pages, www.iclub.net, 2001-2005, 5 pages.
Websters New College Dictionary , Definition of "Virtual Reality", Third Edition, 2005, 3 Pages.
SmartSwing, "SmartSwing Introduces Affordable Intelligent Golf Club", www.smartswinggolf.com , Jan. 2006, 2 pages.
Henrick Arfwedson, et al., "Ericsson's Bluetooth modules", Ericsson Review No. 4, 1999, 8 pages.
ZigBees, "Zigbee information", www.zigbees.com , 2015, 4 pages.
SolidState Technology, "MEMS enable smart golf clubs", www.electroiq.com , 2005, 3 pages.
IGN, "Japanese WII Price Release Date Revealed", www.ign.com , 2006, 1 page.
First Annual Better Golf Through Technology Conference 2006 webpage, www.bettergolfthroughtechnology.com , Massachusetts Institute of Technology, Cambridge Massachusetts, Feb. 2006, 1 page.
Concept2Rowing, "Training" web content, www.concept2.com , 2009, 1 page.
Expresso, Products pages, www.expresso.com/products , 2009, 2 pages.
Manish Kalia, et al., "Efficient Policies for Increasing Capacity in Bluetooth: An Indoor Pico-Cellular Wireless System", IBM India Research Laboratory, Indian Institute of Technology, 2000, 5 pages.
R.Rao, et al., "Demand-Based Bluetooth Scheduling", Pennsylvania State University, 2001, 13 pages.
International Search Report received for PCT Application No. PCT/US2012/065716, dated Jan. 3, 2013, 10 pages.
MyCaddie, 2009, retrieved on Sep. 26, 2012 from http://www.iMakePars.com, 4 pages.
Swing it See it Fix it, Improve Gold Swing, SwingSmart Golf Analyzer, retrieved on Sep. 26, 2012 from http://www.SwingSmart.com, 2 pages.
Learn how Swingbyte can improve your game, retrieved on Sep. 26, 2012 from http://www.swingbyte.com, 2 pages.
International Search Report received for PCT Application No. PCT/US2011/055173, dated Mar. 6, 2012, 8 pages.
International Search Report received for PCT Application No. PCT/US2011/049461, dated Feb. 23, 2012, 14 pages, 2012.
PCT Search Report, PCT/US2012/029310, dated Sep. 28, 2012, 3 pages.
IPRP, PCT/US2011/049461, dated Mar. 7, 2013, 6 pages.
IPRP, PCT/US2011/058182, dated Apr. 30, 2013, 5 pages.
IPER, PCT/US2011/055173, dated Apr. 25, 2013, 5 pages, (2013).
IPRP, PCT/US2012/065716, dated May 20, 2014, 6 pages.
International Search Report for PCT Application No. PCT/US2013/021999, dated Apr. 30, 2013, 8 pages.
International Search Report for PCT Application No. PCT/US2012/066915, dated Mar. 29, 2013, 10 pages.
International Search Report for PCT Application No. PCT/US2015/26896, dated Jul. 28, 2015, 15 pages.
International Search Report for PCT Application No. PCTUS2015/26917, dated Jul. 30, 2015, 16 pages.
The Nike+FuelBand User's Guide, rev 14, 26 pages, 2012.
UP by Jawbone Extended User Guide, 10 pages, 2012.
Armour39, Under Armour Guarantee, Getting Started, retrieved from the Internet on Jul. 12, 2013, 7 pages.
Armour39 Module & Chest Strap, retrieved from the Internet on Jul. 12, 2013, 6 pages.
MiCoach Pacer User Manual, 31 pages, (2009).

Foreman et al. "A Comparative Analysis for the Measurement of Head Accelerations in Ice Hockey Helmets using Non-Accelerometer Based Systems," Nov. 19, 2012, 13 pages.
Reebok-CCM and MC10 to Launch Revolutionary Sports Impact Indicator, MC10 News (http://www.mc10inc.com/news/), Oct. 24, 2012, 3 pages.
CheckLight MC10 Overview, Reebok International Limited, Nov. 20, 2012, 7 pages.
Reebok and MC10 Team Up to Build CheckLight, a Head Impact Indicator (Hands-on), MC10 News (http://www.mc10inc.com/news/), Jan. 11, 2013, 1 pg.
Trace—The Most Advanced Activity Monitor for Action Sports, webpage, retrieved on Aug. 6, 2013, 22 pages.
CheckLight, Sports/Activity Impact Indicator, User Manual, 13 pages, 2013, Reebok International Limited.
King, The Design and Application of Wireless Mems Inertial Measurement Units for the Measurement and Analysis of Golf Swings, 2008.
Grober, An Accelerometer Based Instrumentation of the Golf Club: Comparative Analysis of Golf Swings, 2009.
Gehrig et al, Visual Golf Club Tracking for Enhanced Swing Analysis, Computer Vision Lab, Lausanne, Switzerland, 2003.
PocketPro Golf Designs, PocketPro Full Swing Analysis in Your Pocket, www.PocketPro.org, (2011).
Clemson University, Golf Shot Tutorial, http://www.webnucleo.org/home/online_tools/newton/0.4/html/about_this_tool/tutorials/golf_1.shp.cgi, retrieved on Nov. 10, 2011.
MiCoach Speed_Cell TM, User Manual, 23 pages, (2011).
Nike+iPod, User Guide, 32 pages (2010).
SureShotGPS SS9000X, Intelligent Touch, Instruction Manual, 25 page, 2011.
ActiveReplay, "TRACE—The Most Advanced Activity Monitor for Action Sports", http://www.kickstarter.com/projects/activereplay/trace-the-most-advanced-activity-monitor-for-actio, 13 pages, Oct. 1, 2013.
Zepp Golfsense@Launch2011, https://www.youtube.com/watch?v=VnOcu8szjIk (video), Mar. 14, 2011.
Epson US Newsroom, "Epson America Enters Sports Wearables Market with Introduction of M-Tracer MT500GII Golf Swing Analyzer", www.news.epson.com, Jan. 5, 2015, 4 pages.
International Search Report and Written Opinion dated Dec. 22, 2015 received in PCTUS1561695, 7 pages.
Search Report Received in PCT2013021999 dated Jan. 21, 2016.
International Search Report and Written Opinion mailed in PCTUS1642674 dated Aug. 12, 2016, 9 pages.
International Search Report and Written Opinion received in PCT/US2017/52114, dated Oct. 3, 9 pages.
International Search Report and Written Opinion Received in PCT/US2017/37987, dated Nov. 9, 2017, 12 pages.
Supplementary Extended European Search Report received in 11820763.8 dated Nov. 13, 2017, 16 pages.
Supplementary Extended European Search Report received in 11833159.4 dated Nov. 6, 2017, 14 pages.
Supplementary Partial European Search Report received from EP Application Serial No. 11820763.8, dated Aug. 8, 2017, 15 pages.
Supplementary Partial European Search Report received from EP Application Serial No. 1833159.4, dated Aug. 8, 2017, 15 pages.
David E. Culler, Et al., "Smart Sensors to Network the World", published in Scientific American Magazine, No. 06/2004, dated Jun. 1, 2004, pp. 85-91.
International Search Report and Written Opinion received in PCT/US2017/039209, dated Aug. 24, 2017, 7 pages.
Supplementary Extended European Search Report received in 15782595.1 dated Nov. 27, 2017, 5 pages.

\* cited by examiner

AIMING FEEDBACK SYSTEM WITH INERTIAL SENSORS

BACKGROUND OF THE INVENTION

Field of the Invention

One or more embodiments of the invention are related to the field of motion capture data analysis using sensor data. More particularly, but not by way of limitation, one or more embodiments of the invention enable an aiming feedback system that uses inertial sensor data to measure the direction an object is aimed and to provide feedback to improve or correct the aim.

Description of the Related Art

Systems to measure the position and orientation of an object using inertial sensors are known in the art. For example, inertial guidance systems are widely used in navigation. The increasing availability of low-cost sensors has led to consumer applications that track position, orientation, and motion of users and of equipment. For example, inertial sensors to measure the position, orientation, and motion of a golf club are known in the art.

In many applications, the orientation of an object relative to a target position is of major importance. For example, in golf, a golfer must align the golf club so that the face of the club is pointing towards the hole. While an inertial sensor on the club may provide information about the club's orientation, this sensor alone cannot determine whether the club is aligned correctly relative to the target. It is therefore necessary to supplement inertial sensor information with other data to determine alignment to a target. In addition, it is desirable to have a convenient feedback mechanism to provide feedback to a user so that the user can adjust the aim to align it with the target. There are no known systems based on inertial sensors that provide aiming feedback to a user to assist the user in aligning the aim of an object to a target.

For at least the limitations described above there is a need for an aiming feedback system with inertial sensors.

BRIEF SUMMARY OF THE INVENTION

One or more embodiments described in the specification are related to an aiming feedback system with inertial sensors. Embodiments of the invention use inertial sensor data, possibly supplemented with other information, to determine the relative orientation of an object to a target direction. Feedback on the alignment of the object to the target direction is provided to the user aiming the object. Illustrative applications include for example aiming of sporting equipment, such as clubs, bats, and rackets. In golf, in particular, a golfer may need to align the aim of the clubface with the direction to the hole; embodiments of the system may for example use inertial sensors on the club to determine alignment to the hole and to help the golfer adjust the aim accordingly.

One or more embodiments of the invention enable an aiming feedback system with inertial sensors. Inertial sensors are coupled to an object that may be aimed at a target. The object may have for example a forward direction vector that may depend on the geometry of the object; for example, the forward direction vector for a golf club may be the normal vector to the clubface. Inertial sensor data from the object is transmitted to a processor, which uses this data to determine the orientation of the object's forward direction vector. The processor also receives, obtains, or calculates a target direction vector that indicates the direction to the target. For example, in a golf application the target may be a golf hole, and the target direction vector may point from the club towards the hole. The processor calculates a rotation between the object's forward direction vector and the target direction vector, and it generates an aim alignment signal that provides information on how to align the forward direction vector with the target direction vector.

The aim alignment signal is transmitted to one or more feedback elements that generate feedback signals for a user to assist the user in correcting the aim. One or more embodiments may use feedback elements that include for example, without limitation, displays, optical devices, speakers, and haptic feedback systems. Display feedback elements may for example display text or graphics that indicate the current aim direction, the target direction, the rotation between them, or how to modify the aim to point at the target. Speaker feedback elements may for example generate audio signals that vary with the aim, such as for example a tone or beat that varies as the aim gets closer to the target direction. Speakers may also generate spoken messages that tell the user how to rotate the aim to align it with the target direction; these messages may for example include both a desired direction of rotation (such as left or right) and an angular magnitude. Haptic feedback systems may provide for example taps or vibrations that vary with the aim, or that encode instructions on how to modify the aim to point at the target. Haptic feedback may be integrated for example into a smart watch or a wrist band worn by the user aiming the object. Feedback signals, such as for example audio or haptic signals, may have frequencies or amplitudes that vary with the desired rotation to align the aim with the target direction. For example, the amplitude or frequency of the signal may vary monotonically with the angular magnitude of the rotation between the target direction and the current aim. In addition, the amplitude or frequency may vary to indicate the direction of the desired rotation to align the aim with the target direction.

In some applications the user's goal may be align the projections of the forward direction vector and the target direction vector onto a plane, such as the horizontal plane, rather than to align the vectors themselves. For example, in golf, the forward direction vector for a club typically points upwards because of the loft of the club face; however, the golfer wants to align the horizontal component of this vector with the horizontal vector pointing towards the hole. Therefore, in one or more embodiments the processor may project one or both of the forward direction vector and the target direction vector onto a plane before calculating the rotation between them.

One or more embodiments may use any convenient method to obtain, receive, or calculate the target direction vector. In particular, one or more embodiments may use the object itself to determine the direction to the target. An object may have a designated targeting axis that may be used to point at the target. For example, a user may point the shaft of a golf club at the hole to determine the direction to the hole. When the object's targeting axis is pointed at the target, the inertial sensor data received from the object may be used to calculate the target direction vector. One or more embodiments may include a laser pointer aligned with the targeting axis to assist the user in pointing the targeting axis at the target. The object may then be placed in its normal use orientation and aimed by the user. The system obtains inertial sensor data from the object again, while it is in the normal use orientation, and calculates the forward direction vector that represents the current aim. In one or more embodiments the inertial sensor on the object may also be used to determine the slope of the ground; this information may be useful for example for a golfer who adjusts the swing based on the slope. The object may for example be placed on the ground with its targeting axis pointing horizontally towards the target; the inertial sensor data received in this orientation may be used to calculate the slope of the ground. The system may then provide slope information to the user along with feedback information on the aim relative to the target.

BRIEF DESCRIPTION OF THE DRAWINGS

The above and other aspects, features and advantages of the invention will be more apparent from the following more particular description thereof, presented in conjunction with the following drawings wherein.

DETAILED DESCRIPTION OF THE INVENTION

An aiming feedback system with inertial sensors will now be described. In the following exemplary description numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Figure 1:
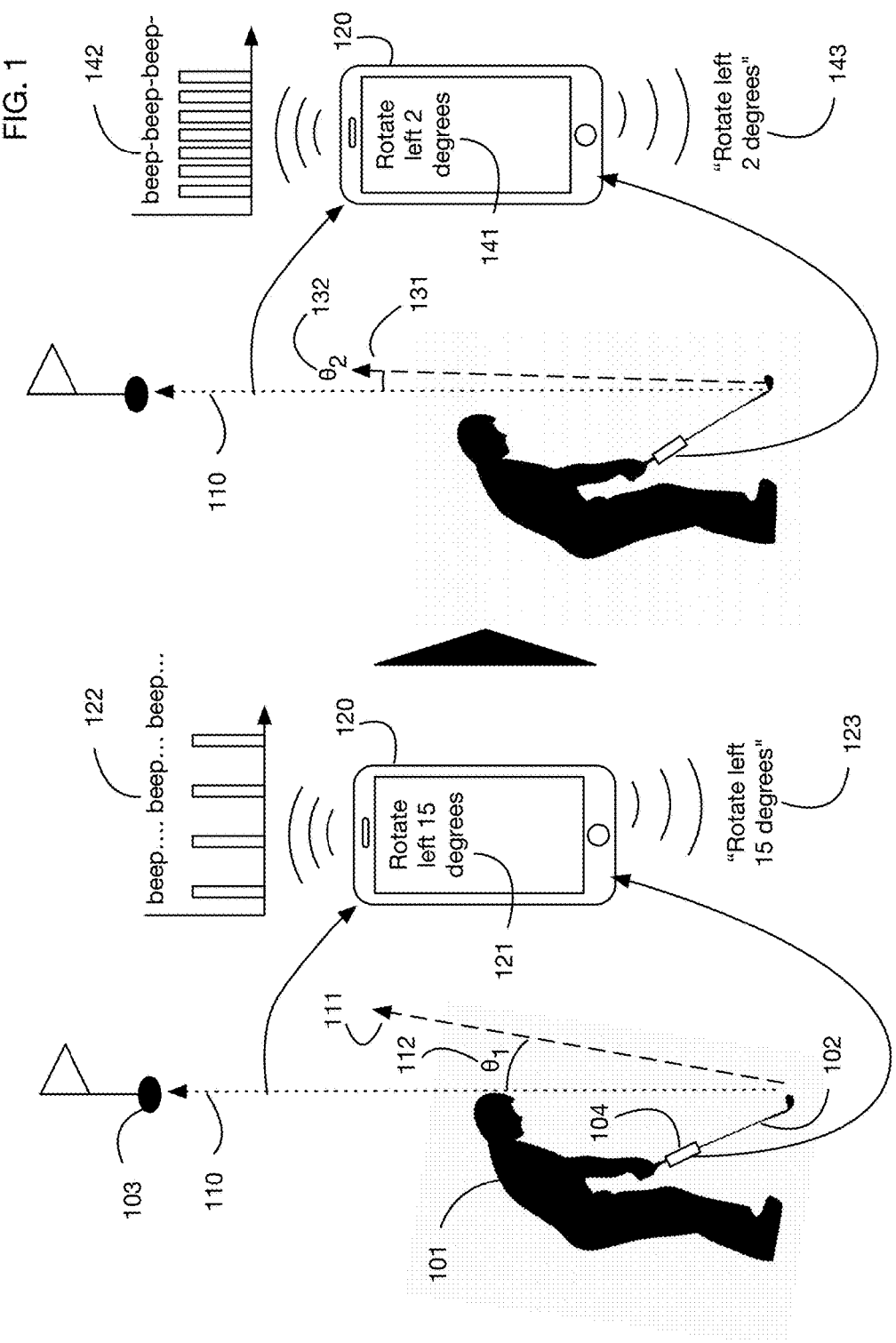
FIG. 1 illustrates an embodiment of the system that provides aim correction feedback to a golfer who aims a golf club at a golf hole.

FIG. 1 illustrates an embodiment of the system that provides aiming feedback to a golfer. This example is illustrative; one or more embodiments may provide aiming feedback for any object, including but not limited to objects used for sports. In the embodiment shown, user 101 wants to aim the golf club 102 so that the ball travels in the target direction 110 towards the hole 103. An inertial sensor 104 is attached to the golf club 102, providing data on the position and orientation of the club. This inertial sensor data is transmitted to mobile device 120. In this example, the inertial sensor 104 contains a wireless transmitter to transmit data to mobile device 120. One or more embodiments may use any methods to transmit sensor data to any other device, over wired or wireless networks or combinations thereof. Device 120 calculates the current aim direction 111 of the golf club 102 from the inertial sensor data generated by sensor 104. Device 120 also receives, generates, calculates, or estimates the target direction vector 110. Embodiments may use various methods to determine, receive, calculate, estimate, or obtain this target direction vector. For example, in some situations the location of the target 103 may be known in advance, in which case knowledge of the position of the object to be aimed (such as golf club 102) is sufficient to calculate the target direction vector 110. In other situations, sensors may be used to determine the direction to the target. As described below, in one or more embodiments the object to be aimed may also serve as a sensor to acquire the target direction vector 110.

Device 120 determines the rotation 112 between the desired aim (target direction vector 110) and the actual aim (forward direction vector 111). It uses this rotation to provide feedback to the user 101 on how closely the aim is aligned with the target, or on specific corrections to the aim needed to align it with the target. In the example of FIG. 1, device 120 displays message 121 on the screen providing specific aim correction instructions. The device may also provide audio feedback, haptic feedback, or more generally feedback using any type of signal or signals. Audio or haptic feedback signals provide the potential benefit that the user 101 does not need to look away from the object he or she is aiming to receive the feedback. In FIG. 1, device 120 also provides audio feedback. Two types of audio feedback are shown: the device may provide a voice command 123, similar to the display message 121; the device may also or in addition provide signals such as tones or beeps 122 that indicate how close the aim is to the target direction. In the example shown, the beeps are infrequent when the aim is far away from the target direction, and they grow more frequent as the aim approaches the target direction. This scheme is illustrative; one or more embodiments may use any feedback signals to compare the aim to the target direction or to suggest aim changes.

As the user changes the aim of the golf club 102, the device 120 changes the feedback signals to reflect the updated aim. The user can therefore continue adjusting the aim until it is aligned with the target. In the right side of FIG. 1, the user has shifted the aim of the golf club so that the new forward direction vector 131 is closer to the target direction vector 110. The inertial sensor sends updated sensor data to the device 120, and the device calculates the updated rotation 132 between the vectors 131 and 110. The device then updates the feedback signals 141, 143, and 142. In particular, the audio feedback 142 increases the frequency of the beeps, telling the golfer that the aim is closer to the target. In one or more embodiments the frequent beeps may be replaced for example with a continuous tone when the aim is fully aligned with the target (or within a specified tolerance of the target direction vector). In one or more embodiments beeps or other signals may instead decrease in frequency as the aim approaches the target direction, for example with the signal becoming silent when the aim is perfectly aligned with the target.

Figure 2:
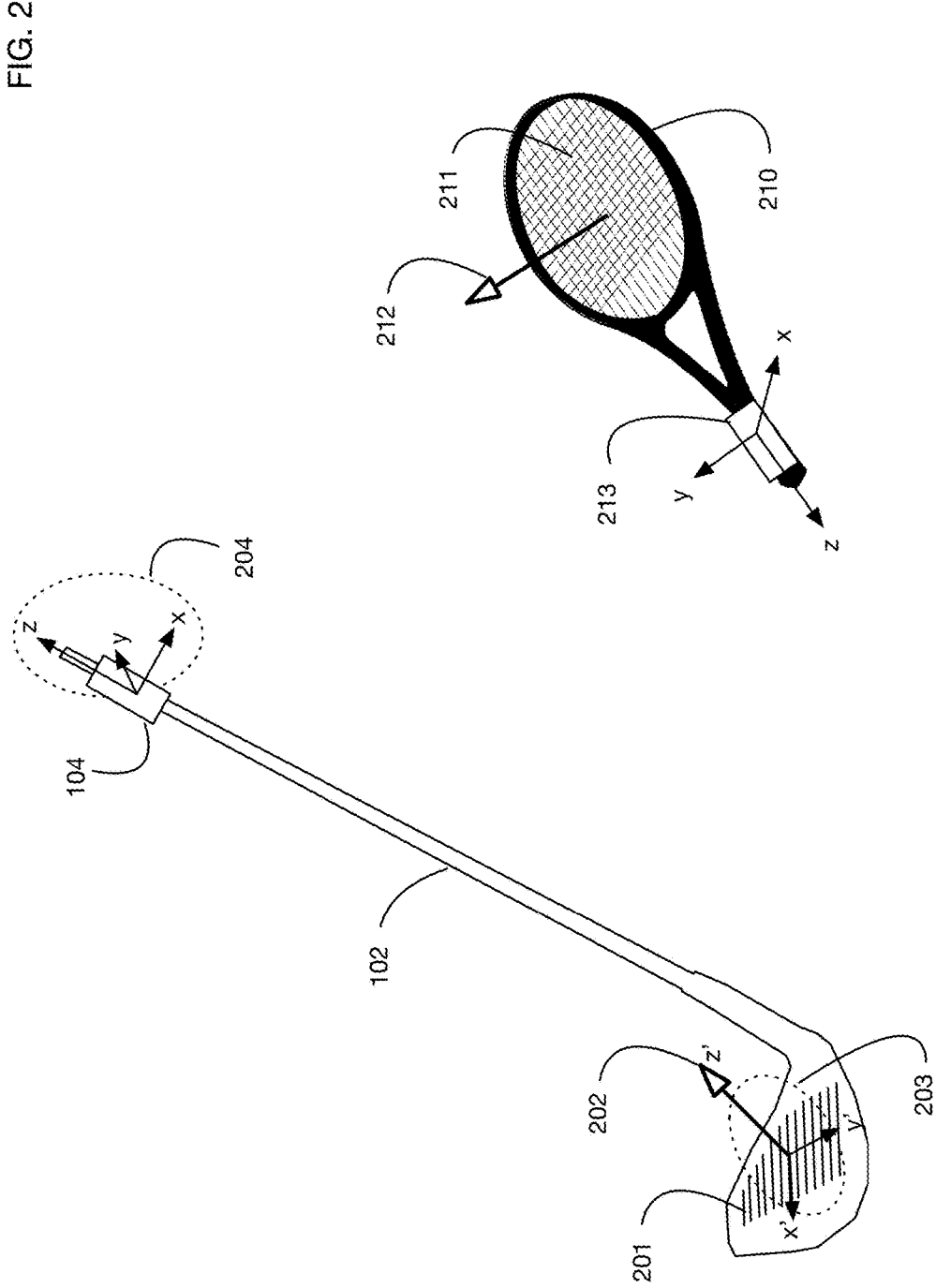
FIG. 2 illustrates forward direction vectors associated with a golf club and a tennis racket, corresponding to the direction in which a ball will be launched when hit, and shows illustrative reference axes of inertial sensors attached to the club and the racket.

As mentioned above, one or more embodiments of the invention may be used to provide feedback for the aiming of any object. FIG. 2 shows two objects that are equipped for aiming feedback: golf club 102 (as in FIG. 1), and tennis racket 210. In each case the object has a forward direction vector associated with the geometry of the object. For golf club 102, forward direction vector 202 is the normal vector to the clubface 201. For tennis racket 210, forward direction vector 212 is the normal vector to the racket face 211. Any vector may be selected as a forward direction vector for an object. The forward direction vector may in some cases correspond to the direction that a ball is launched, but in general it may be any desired direction associated with an object. In one or more embodiments there may be multiple forward direction vectors associated with the object, and a specific forward direction vector may be selected for aiming feedback based on context or on other data. For example, racket 210 may be used in either forehand or backhand direction, with opposing forward direction vectors.

In one or more embodiments one or more inertial sensors or other types of sensors may be coupled to or embedded in an object to be aimed. For example, inertial sensor 104 is attached to golf club 102, and inertial sensor 213 is attached to racket 210. Inertial sensors may be attached to any location of an object and in any orientation. In one or more embodiments inertial sensors or other sensors may be attached to an object at multiple different locations. To support aiming feedback, it is generally necessary to obtain or determine the relationship between the position and orientation of the inertial sensor or sensors and that of the forward direction vector for the object. Presuming that the object being aimed is a rigid body or an approximately rigid body, there is a fixed relationship between the position and orientation of the inertial sensors on the object and the position and orientation of the forward direction vector. This relationship may be determined for example via calibration methods when the inertial sensor is installed onto the object. In general, there is a transformation between the reference frame of the inertial sensor and the reference frame associated with the forward direction vector. For example, for golf club 102, the sensor reference frame 204 may be at or near the grip of the golf club, while the forward direction reference frame 203 may be associated with the clubface. As is known in the art, a transformation comprising a rotation and a translation may be performed to transform the sensor reference frame into the forward direction reference frame, or vice versa. The transformation is a characteristic of the object's geometry, the selected forward direction vector, and the installed location and orientation of the sensors.

Figure 3:
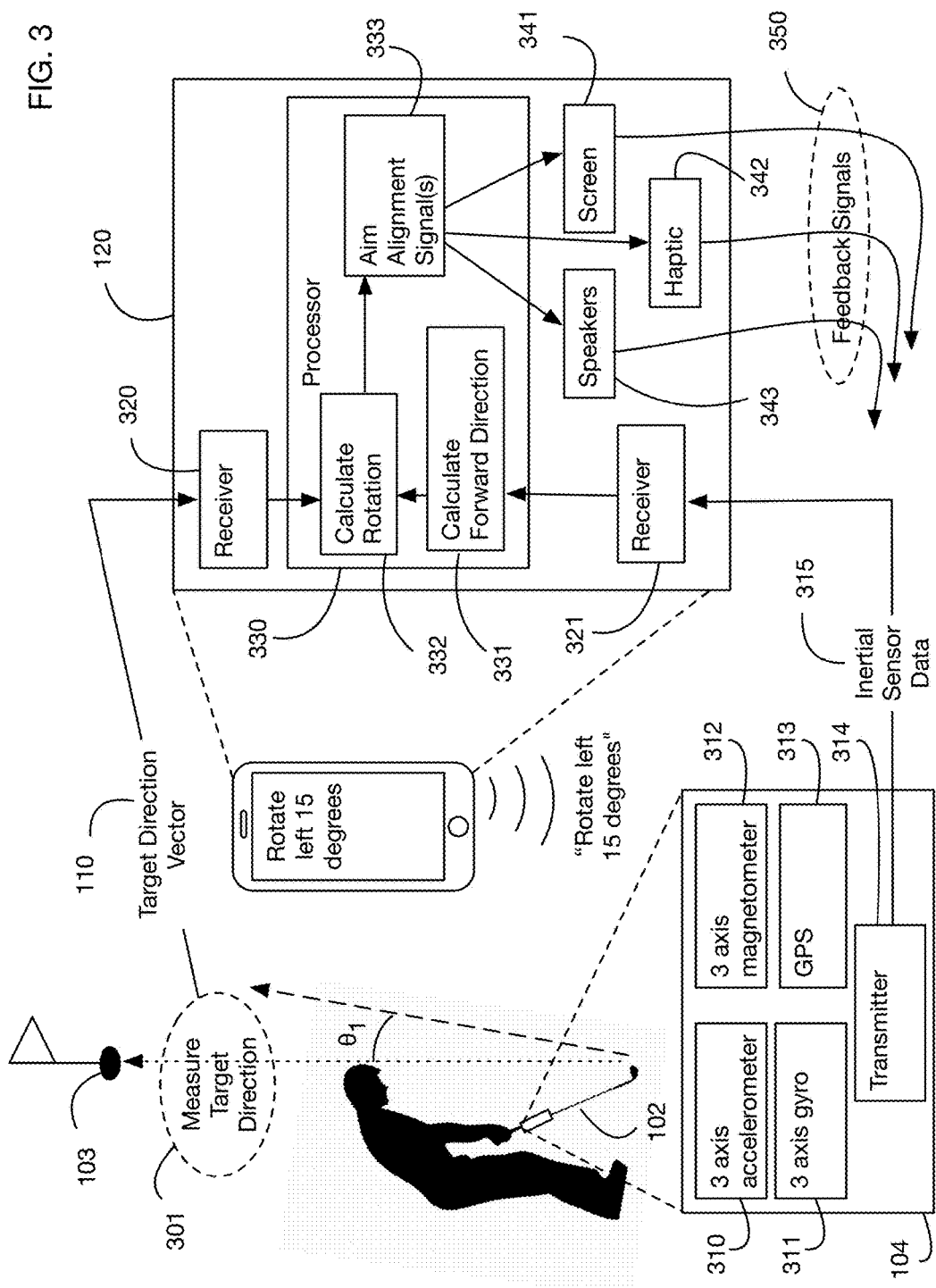
FIG. 3 shows an architectural block diagram of the components of the system illustrated in FIG. 1.

FIG. 3 shows an architectural block diagram of the components of the embodiment shown in FIG. 1. Inertial sensor module 104 may contain any types of sensors. For illustration, FIG. 3 shows possible sensors that include a 3 axis accelerometer 310, a 3 axis gyroscope 311, a 3 axis magnetometer 312, and a GPS 313. Any or all of these sensors are optional. Any or all of these sensors may have any number of axes, including but not limited to three axes. One or more embodiments may use additional sensors that are not illustrated. Any sensor or sensors that provide information on the position or orientation of the object, or on any changes to position or orientation, may be used by one or more embodiments.

Data 315 from the inertial sensors (or other sensors) 310, 311, 312, 313 are transmitted by transmitter 314 to a receiver 321, which is coupled to a processor 330 that analyzes the sensor data. The connection between the inertial sensor module transmitter 314 and the receiver 321 may be wired or wireless, using any desired network protocols and media. In one or more embodiments the processor that analyzes the sensor data may be integrated into the same physical device as the inertial sensors. In one or more embodiments the processor may be remote from the inertial sensors.

Device 120 in FIG. 1 is a mobile device that contains a processor, a network receiver, and feedback devices such as a display and speakers. In one or more embodiments these functions may be separated into different devices. For example, a processor that analyzes sensor data may be in a different device than the device that generates feedback signals. In one or more embodiments the inertial sensor or sensors, the processor, and the feedback elements may all be integrated into a single device. For illustration, in FIG. 3 device 120 contains multiple components: a receiver 321 that receives inertial sensor data 315, a receiver 320 that receives the target direction vector 110, a processor 330 that analyzes the data, and feedback elements 341, 342, and 343. The receivers 321 and 320 may be identical elements or they may be different. In one or more embodiments the processor 330 may be a single processor, a multiprocessor, a network of processors, or a specialized circuit. In one or more embodiments the processor or processors may be for example a microprocessor, a mobile device, a personal computer, a laptop computer, a desktop computer, a tablet computer, a smart phone, a smart watch, a server, or a network of any of these devices.

Target Direction Vector 110 is obtained via process 301, and is transmitted to receiver 320. Transmission of target direction vector 110 may be over a wired or wireless network, using any desired protocols and media. One or more embodiments may use any methods, hardware, and software to implement the Measure Target Direction process 301. For example, in one or more embodiments the target direction to a target may be obtained from a database containing the location of known targets. For instance, in a golf application, targets at a golf course or a driving range may be in fixed, known locations, and device 120 may obtain these locations directly from a database when the golfer is at that site. In one or more embodiments the user may use one or more sensors to perform the step 301. In one or more embodiments the targets themselves may be instrumented with sensors, and the step 301 may comprise retrieving this target sensor data to obtain the target locations.

Processor 330 analyzes the inertial sensor data 315 and the target direction vector 110 to determine how closely the object aim is aligned with the target direction. It calculates the forward direction 331 of the object from the inertial sensor data 315 to determine the direction in which the object is currently aimed. The specific calculations of this step 331 depend on the types of sensors included in sensors 104. For example, if sensors 104 include accelerometer 310 and magnetometer 312, and if the object 102 is not accelerating, then the orientation of the object relative to an Earth reference frame may be calculated directly, as is known in the art. (The accelerometer provides the orientation of the sensors relative to the gravity vector, and the magnetometer provides the orientation of the sensors relative to the magnetic field vector.) If for example sensors 104 include accelerometer 310 and gyro 311, then the inertial sensor data 315 may be integrated to obtain the orientation of the sensors relative to any fixed reference frame, provided that an initial orientation is known, as is known in the art. Having obtained the orientation of the sensors, the orientation of the object's forward direction vector may be calculated directly using the fixed transformation between the sensor reference frame and the forward direction reference frame, as described above.

The processor then calculates the rotation 332 between the object's forward direction vector and the target direction vector 110. The angular magnitude of this rotation determines how closely aligned the object's aim is with the target direction. The axis of rotation determines the direction in which the object's aim should be rotated to align the aim with the target direction. Based on the rotation, the processor calculates one or more aim alignment signals 333 that describe the rotation or that provide information on how to align the aim with the target. The processor then transmits these aim alignment signals to one or more feedback elements that generate feedback signals to the user. FIG. 3 shows three feedback elements: screen 341, haptic feedback system 342, and speakers 343. These feedback elements are illustrative; one or more embodiments may use any device or devices to generate feedback. The feedback element or elements generate feedback signals 350 (such as for example sound or vibrations) that are transmitted to the user to assist the user in correcting the aim.

Figure 4:
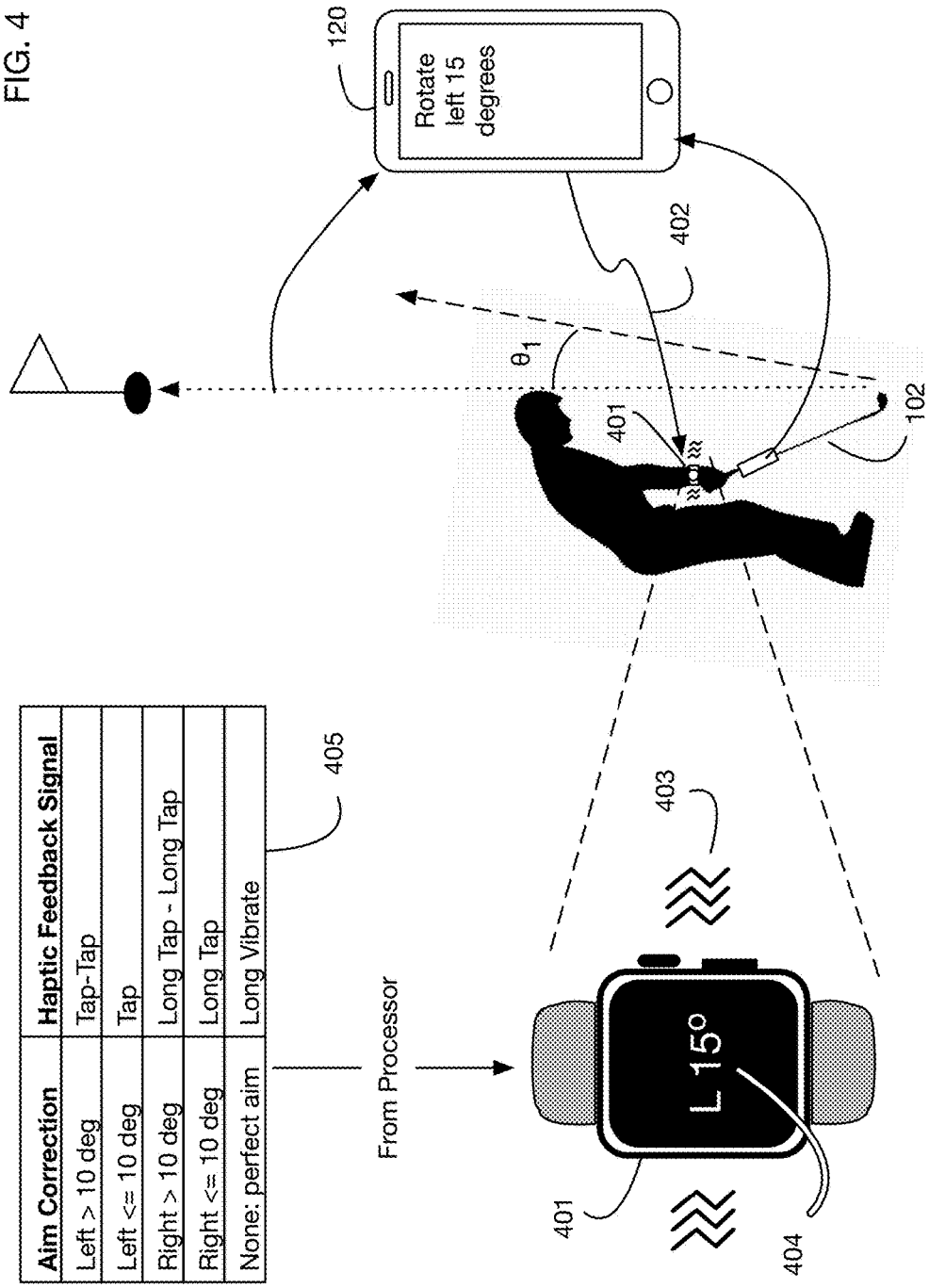
FIG. 4 illustrates an embodiment that provides haptic aiming feedback using a smart watch with a haptic subsystem.

FIG. 4 illustrates an embodiment that includes a haptic feedback system. As in FIG. 1, device 120 receives inertial sensor data from golf club 102 and calculates the alignment between the club's forward direction vector and the target direction. Device 120 displays an aim correction message on the screen. In addition, device 120 transmits a feedback signal 402 to a smart watch 401 worn by the user. The watch 401 has a haptic feedback system that generates taps and vibrations 403 that the user can feel. The watch 401 also displays a message 404 with aim correction information like that shown on device 120. Table 405 shows illustrative haptic feedback signals that indicate the magnitude and direction of the aim corrections needed to align the golf club's aim with the target. These signals are illustrative; one or more embodiments may encode aim correction or aim alignment information into any desired set of haptic feedback signals.

In the embodiment shown in FIG. 4, the processor receiving inertial sensor data is embedded in mobile device 120, which then transmits feedback information to smart watch 401. In one or more embodiments the smart watch 401 may instead (or in addition) receive inertial sensor data directly, and calculate the aim alignment information without requiring the mobile device 120. More generally in one or more embodiments the functions of receiving sensor data, calculating aim alignment, and providing feedback may be distributed across physical devices in any desired manner. In one or more embodiments feedback signals may be provided by multiple devices simultaneously; for example, a user may obtain haptic feedback from a smart watch and audio feedback from a mobile phone at the same time.

Figure 5:
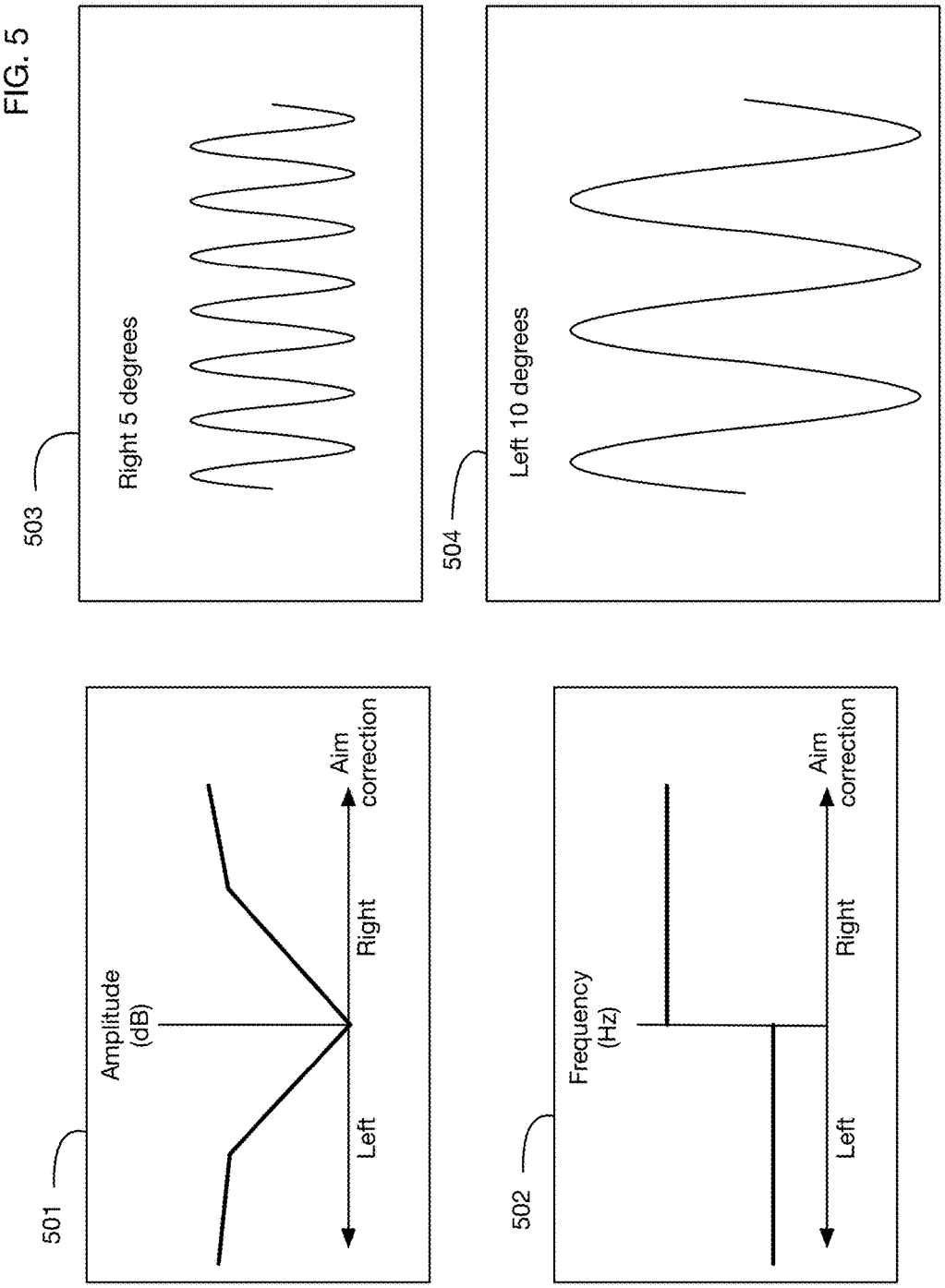
FIG. 5 illustrates an embodiment that encodes aim correction magnitude and direction in the amplitude and frequency, respectively, of a feedback signal generated by the system.

One or more embodiments may use any desired functions to encode aim alignment information into feedback signals. FIG. 5 illustrates an embodiment that encodes the magnitude and direction of aim corrections into the amplitude and frequency, respectively, of a feedback signal. The feedback signal may be, for example, an audio signal, a vibration or tapping haptic signal, or a flashing light signal. The signal may vary in magnitude and frequency to indicate the required aim corrections. In the example of FIG. 5, the amplitude 501 increases monotonically with the magnitude of the aim correction. In this example a higher magnitude indicates a larger aim correction. One or more embodiments may employ the opposite convention of associating a larger signal amplitude with a smaller aim correction. The frequency 502 in this example has two different values that indicate whether the aim needs to be corrected to the left or to the right. In this example a high frequency signal indicates that the aim should be corrected to the right; a low frequency signal indicates that the aim should be corrected to the left. One or more embodiments may use other encoding schemes to indicate an arbitrary axis around which the forward direction vector should be rotated to bring it into alignment with the target direction vector. FIG. 5 shows examples of the feedback signal scheme defined by 501 and 502: signal 503 is a high frequency, lower amplitude signal indicating an adjustment to the right by 5 degrees; signal 504 is a low frequency, higher amplitude signal indicating an adjustment to the left by 10 degrees.

Figure 6:
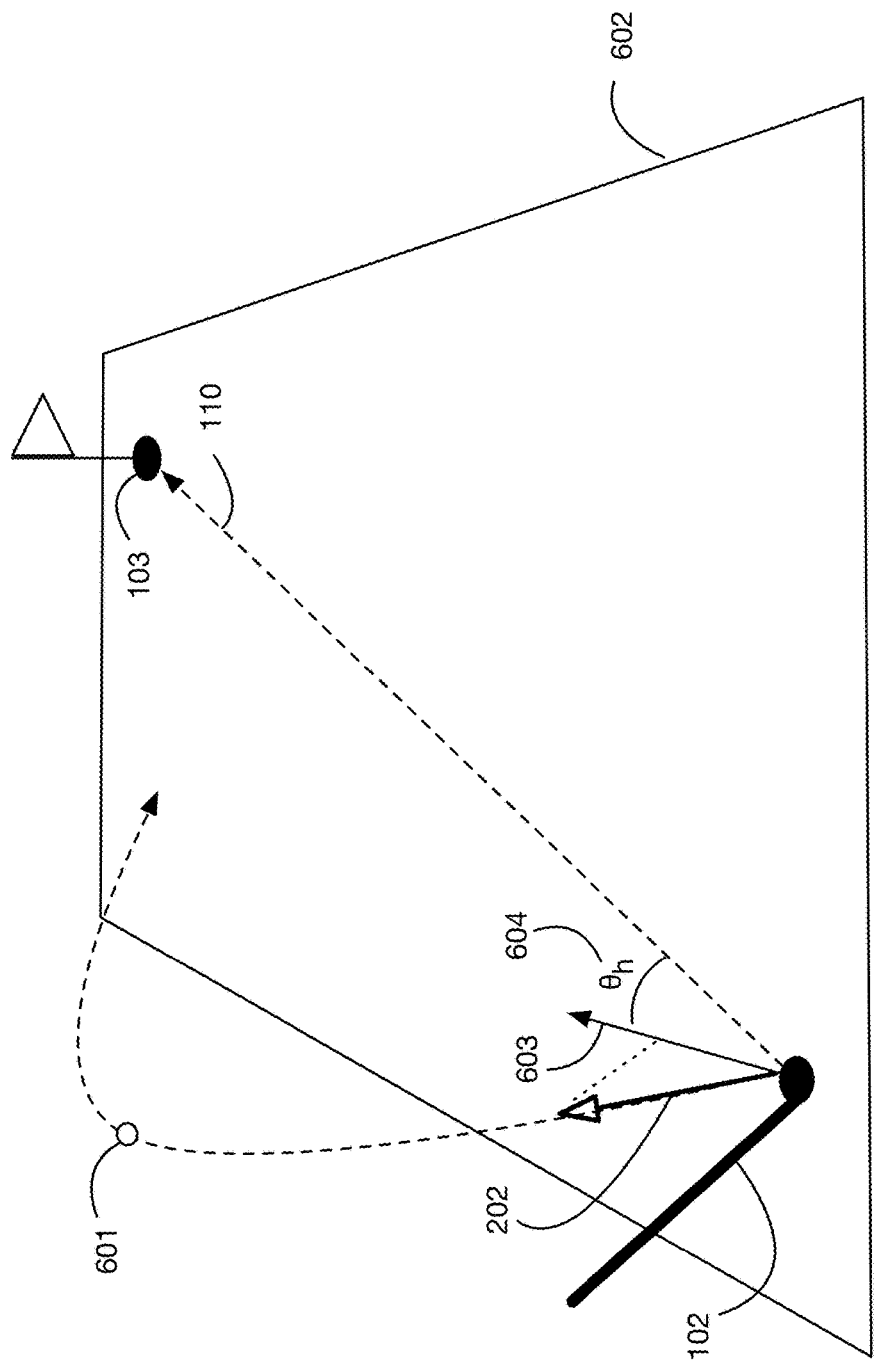
FIG. 6 illustrates an embodiment that projects the forward direction vector, in this case the normal to a golf clubface, onto the horizontal plane, and compares this horizontal projection to the direction to the target.

In one or more embodiments an aim adjustment may be based for example on the components or projections of the forward direction vector and the target direction vector onto a plane or a line, rather than on the original vectors themselves. FIG. 6 illustrates such an embodiment for a golf application. In golf the forward direction vector of a golf club, which is for example normal to the clubface, typically has an upward vertical component as well as a horizontal component since the club often is designed to launch the ball into the air. However, the aim adjustment to aim towards the hole may primarily involve adjusting the horizontal component of the aim. In FIG. 6, club 102 has a forward direction vector (normal to the clubface, for example) 202, which sends ball 601 into the air. The projection of this vector onto the horizontal ground plane 602 is vector 603. The aim adjustment may be based for example on angle 604 between the horizontal forward direction vector 603 and the target direction vector 110. In this example the target direction vector 110 is assumed to lie on the plane 602. In one or more embodiments the target direction vector may also be projected onto a plane to determine an aim correction.

Figure 7:
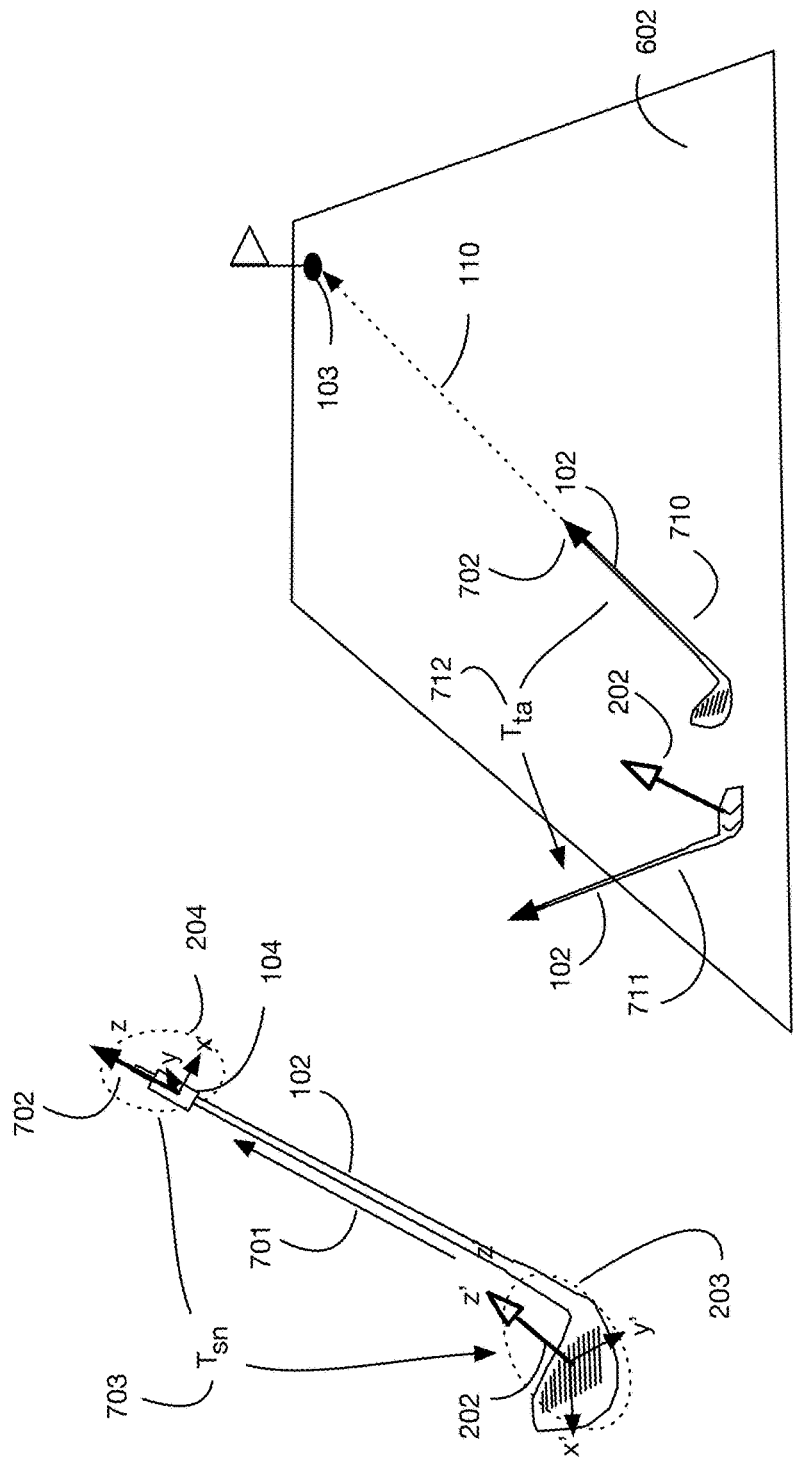
FIG. 7 shows an embodiment that uses the shaft of a golf club to determine the direction to the target.

We now describe a method for obtaining the target direction vector using the same object whose aim is adjusted towards the target. In one or more embodiments the object may have targeting axis that can be pointed at the target. This targeting axis may be different from the forward direction vector of the object. FIG. 7 illustrates an example using a golf application. Golf club 102 has forward direction vector 202, which is normal to the clubface. The shaft of the club defines a targeting axis 701. When a user points the shaft at the target, the system can obtain the target direction vector using the inertial sensor attached to the club. In FIG. 7, the z axis 702 of the inertial sensor 104 is aligned with the shaft axis 701; therefore, the orientation of this z-axis provides the target direction vector. This configuration is illustrative; one or more embodiments may use any position and orientation of an inertial sensor and translate from this position and orientation to the targeting axis in order to obtain the target direction vector. As described above, the specific calculations required to obtain the target direction vector from the inertial sensor data may depend on the types of sensors available. For example, if the sensors 104 include a 3 axis accelerometer and a 3 axis magnetometer, the orientation of the inertial sensor relative to the Earth reference frame may be obtained directly; hence the target direction vector may be calculated directly using the known relationship between the sensor reference frame and the targeting axis.

The right side of FIG. 7 illustrates a targeting procedure that may be used in one or more embodiments. The user places the golf club 102 on the ground in orientation 710, with the shaft pointing towards the target 103. The system obtains inertial sensor data while the club is in this orientation, and calculates the target direction vector using the orientation of the z-axis 702, which is aligned (in this example) with the targeting axis. The user then rotates (and possibly translates) the club to orientation 711 to make the shot. By tracking and integrating the inertial sensor data during this motion, the system can calculate the transformation 712 between the targeting orientation 710 and the aiming orientation 711. Thus the orientation of the forward direction vector 202 relative to the target direction can be calculated. Specifically, in the sensor reference frame 204 in orientation 710, the target direction vector 110 is aligned with the z axis 702; thus the vector 110 in this frame is k (the unit vector in the z direction). If we represent the transformation 712 between 710 and 711 as $T_{ta}$ (ta=targeting to aiming), and the transformation 703 between the sensor reference frame 204 and the clubface reference frame 203 as $T_{sn}$ (sn=sensor to normal), then the target direction vector relative to the clubface frame 203 is $T_{sn}T_{ta}k$. The forward direction vector in the clubface frame is simply k. Thus the rotation between the forward direction vector 202 and the target direction vector 110 is the rotation that rotates k into $T_{sn}T_{ta}k$, which can be calculated directly.

Figure 8:
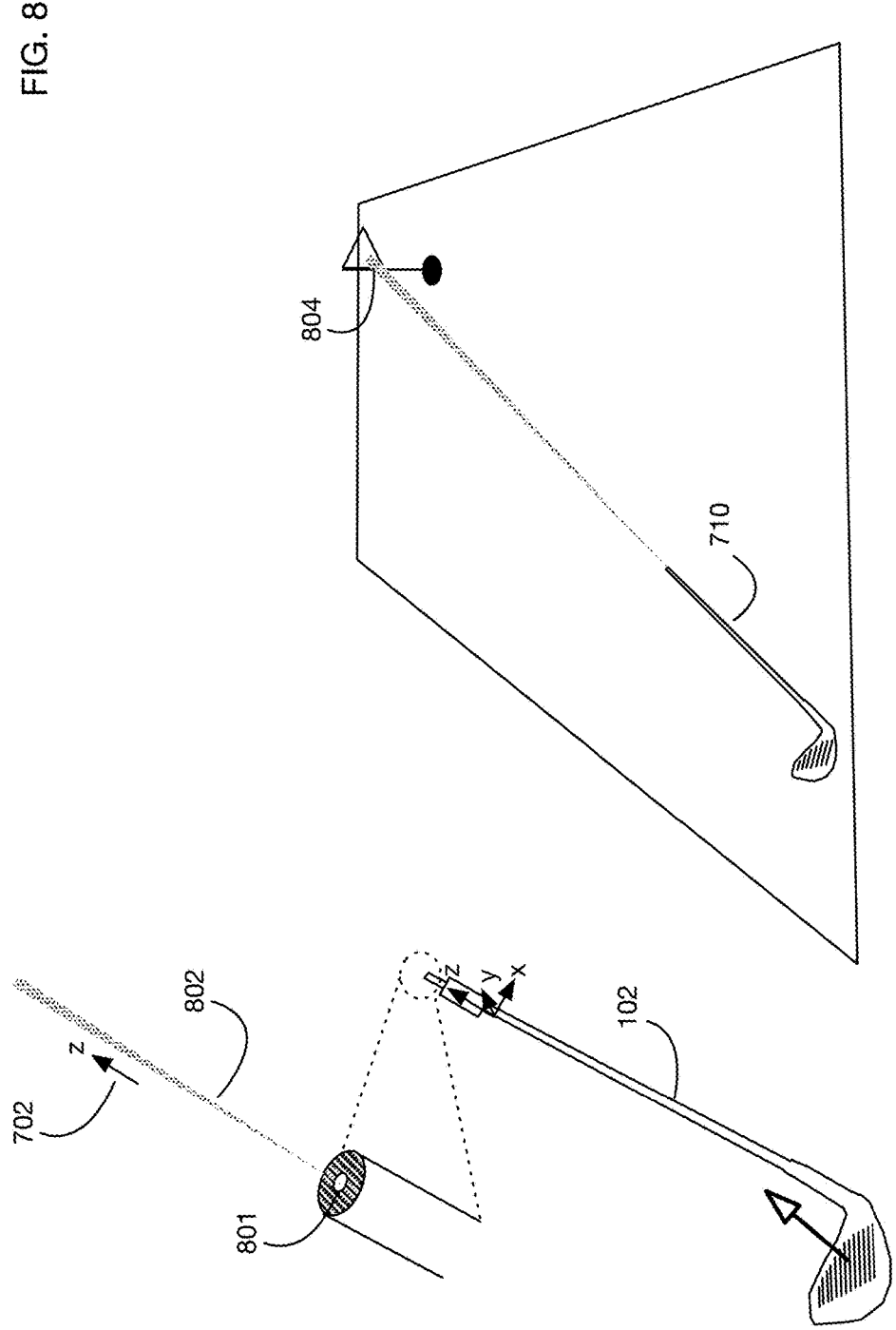
FIG. 8 extends the example of FIG. 7 with an embodiment that has a laser pointer attached to or embedded in the shaft of the golf club, to assist in pointing at the target.

In one or more embodiments a laser pointer or other pointing device may be attached to the object and aligned with the object's targeting axis, to assist the user in pointing at the target. FIG. 8 illustrates an example with a laser pointer 801 installed in the grip of the golf club, so that a laser beam 802 is emitted along the targeting axis 702. The user may place the club in orientation 710 so that the laser beam 802 hits at or near the target, for example on the flag at location 804. The target direction calculation procedure described above may then be performed to acquire the target direction vector.

Figure 9:
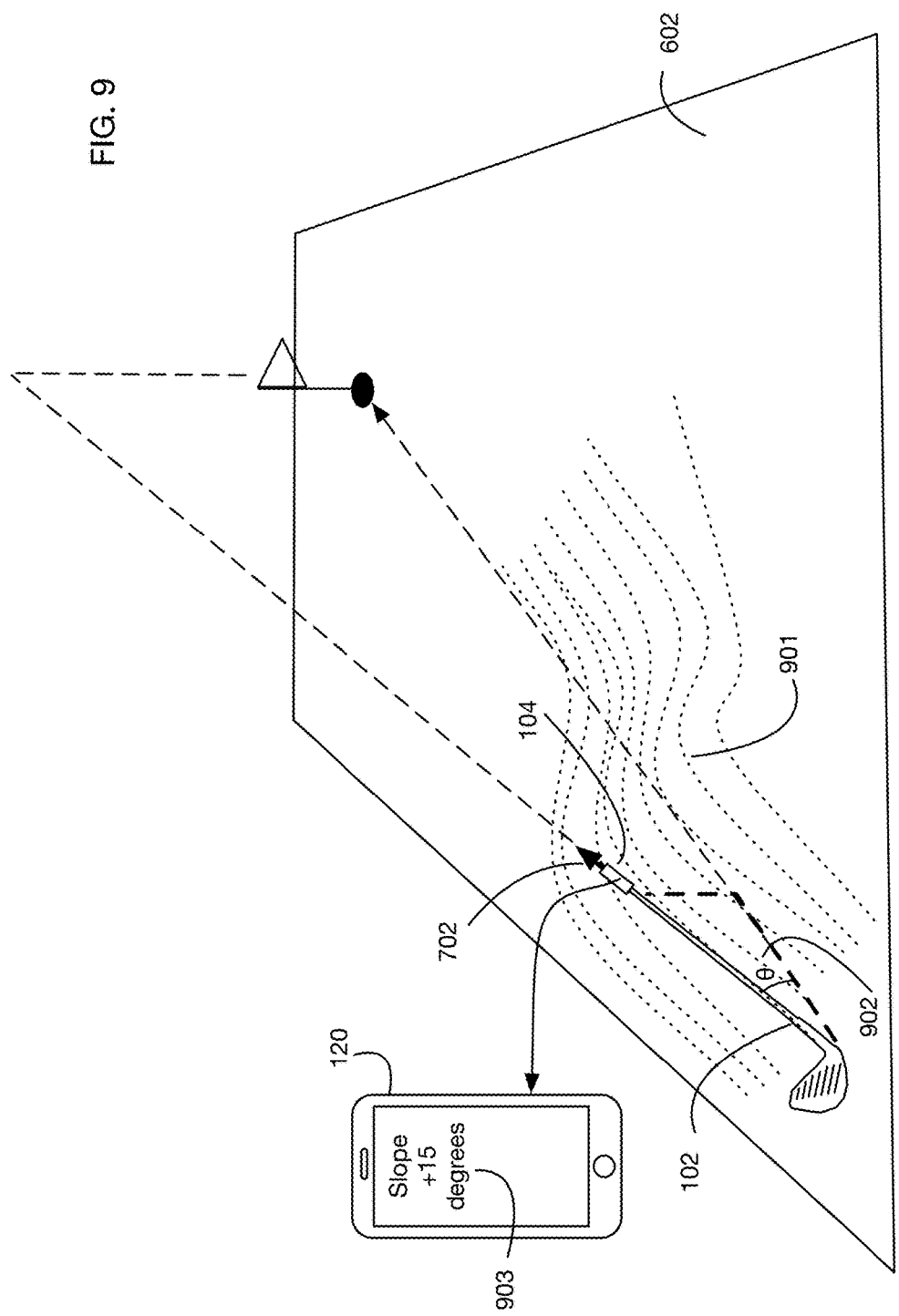
FIG. 9 shows an embodiment that provides feedback on the slope the ground when the shaft of a golf club is placed on the ground.

One or more embodiments may also use the procedures described in FIGS. 7 and 8 to determine the slope of the ground in an area where the object is being aimed, or in any other area where a slope reading is desired. This information may be useful for example in golf, since the slope may affect how the golfer hits a shot. FIG. 9 illustrates an example with club 102 placed on a sloped region 901, such that the targeting vector 702 (aligned with the shaft of the club) points towards the target horizontally, but points upwards because of the slope. Inertial sensor data from sensor 104 can provide a measurement of the slope angle 902, for example by using accelerometer values on three axes to determine the orientation of sensor 104 relative to the vertical gravity vector. Specifically, presuming that the z-axis of the accelerometer is aligned with targeting axis 702, the angle 902 may be calculated as $\theta = a\sin(\alpha_z/\sqrt{\alpha_x^2+\alpha_y^2+\alpha_z^2})$, where the accelerometer vector is ($\alpha_x$, $\alpha_y$, $\alpha_z$). This information may be displayed for example as message 903 on mobile device 120. Alternatively, or in addition, any of the feedback devices described above may also generate feedback signals that depend on the slope.

While the invention herein disclosed has been described by means of specific embodiments and applications thereof, numerous modifications and variations could be made thereto by those skilled in the art without departing from the scope of the invention set forth in the claims.

What is claimed is:

1. An aiming feedback system with inertial sensors, comprising:
    an inertial sensor configured to be attached to a location on or embedded within an object that is aimed at a target,
        wherein said object comprises a forward direction vector that defines a current aim direction in which said object is currently aimed, wherein said forward direction vector depends on a geometry of said object;
        wherein said object is a piece of sporting equipment with a shaft; and,
        wherein said object further comprises a targeting axis parallel to said shaft,
            wherein said targeting axis is used to orient said object at said target;
    a feedback element configured to
        receive an aim alignment signal; and,
        provide a feedback signal based on said aim alignment signal to a user who uses said object while said object is aimed at said target and while said targeting axis is pointed at said target,
            such that when said user changes said current aim of said object, said feedback element changes said feedback signal as said user changes said current aim of the object to reflect an updated aim; and,
    a processor configured to
        receive an initial inertial sensor data from said inertial sensor, wherein said initial inertial sensor data is captured when said object is oriented such that said targeting axis is oriented at said target;
        calculate a target direction vector from said initial inertial sensor data when said targeting axis is oriented at said target, wherein said target direction vector indicates a desired aim direction to said target;
        receive additional inertial sensor data from said inertial sensor when said object is placed in its normal use orientation and aimed by said user;
        calculate said forward direction vector that defines said current aim direction from said additional inertial sensor data, wherein said current aim direction indicates an actual aim direction in which said object is currently aimed to said target;
        calculate a rotation between said forward direction vector of said object and said target direction vector based on said additional inertial sensor data;
        calculate said aim alignment signal based on said rotation, wherein said aim alignment signal comprises information on how to align said forward direction vector with said target direction vector; and,
        send said aim alignment signal to said feedback element to assist said user in modifying or correcting said current aim direction of said object to said target while said object is aimed at said target.

2. The system of claim 1, wherein
said piece of sporting equipment is a golf club;
said forward direction vector is a normal vector to a clubface of said golf club; and,
said target direction vector points towards a golf hole.

3. The system of claim 1, wherein
said feedback element is a display; and,
said feedback signal is one or more of text and graphics shown on said display.

4. The system of claim 1, wherein
said feedback signal is an audio signal.

5. The system of claim 4, wherein
said audio signal is a spoken message.

6. The system of claim 5, wherein
said spoken message tells said user one or both of
    a direction in which to rotate said object to align said forward direction vector and said target direction vector; and,
    an angular magnitude by which to rotate said object to align said forward direction vector and said target direction vector.

7. The system of claim 1, wherein
said feedback signal is a haptic feedback signal.

8. The system of claim 7, wherein
said feedback element is a watch or a wrist band.

9. The system of claim 1, wherein
said feedback signal comprises a magnitude attribute that increases monotonically or decreases monotonically as a function of an angular magnitude of said rotation between said desired aim direction to said target and said current aim direction.

10. The system of claim 9, wherein said magnitude attribute is one or both of
an amplitude of said feedback signal; and,
a frequency of said feedback signal.

11. The system of claim 1, wherein
said feedback signal comprises a direction attribute that indicates a direction of an axis of said rotation to bring said forward direction vector into alignment with said target direction vector.

12. The system of claim 11, wherein said direction attribute is one or both of
an amplitude of said feedback signal; and,
a frequency of said feedback signal.

13. The system of claim 1, wherein said processor further
projects said target direction vector onto a horizontal plane, yielding a horizontal target direction vector, before said rotation is calculated;
projects said forward direction vector onto said horizontal plane, yielding a horizontal forward direction vector, before said rotation is calculated; and,
calculates said rotation between said horizontal forward direction vector and said horizontal target direction vector.

14. The system of claim 1, further comprising
a laser coupled to said object and configured to project a beam of light in a direction of said targeting axis.

15. The system of claim 1, wherein
said piece of sporting equipment is a golf club;
said forward direction vector is a normal vector to a clubface of said golf club; and,
said targeting axis is an axis along said shaft of said golf club.

16. The system of claim 15, wherein said processor is further configured to
calculate a slope of a ground from said initial inertial sensor data when said shaft of said golf club is placed on said ground; and,
transmit said slope to said feedback element.

17. The system of claim 1, wherein said calculate said target direction vector from said initial inertial sensor data further comprises tracking and integrating said initial inertial sensor data as said piece of sporting equipment is rotated.

18. The system of claim 1, wherein said processor is further configured to perform a transformation between a reference frame of said inertial sensor and a reference frame associated with said forward direction vector.

19. The system of claim 1, wherein said object being aimed serves as a sensor to acquire said target direction vector.

* * * * *